United States Patent [19]

Peterson

[11] 3,980,784

[45] Sept. 14, 1976

[54] CONTROL OF ANIMAL PARASITES WITH BENZIMIDAZOLES

[75] Inventor: Lance George Peterson, Fresno, Calif.

[73] Assignee: Eli Lilly and Company, Indianapolis, Ind.

[22] Filed: June 12, 1975

[21] Appl. No.: 584,991

Related U.S. Application Data

[63] Continuation-in-part of Ser. No. 528,606, Dec. 2, 1974, abandoned, which is a continuation-in-part of Ser. No. 450,128, March 11, 1974, abandoned.

[52] U.S. Cl. ............................................. 424/273
[51] Int. Cl.[2] ....................................... A61K 31/415
[58] Field of Search ..................................... 424/273

[56] References Cited
UNITED STATES PATENTS 3,542,923　11/1970　Newbold et al..................... 424/248

*Primary Examiner*—Sam Rosen
*Attorney, Agent, or Firm*—Joseph A. Jones; Everet F. Smith

[57] ABSTRACT

A class of substituted benzimidazoles are useful parasiticides for the systemic control of insects and acarina which feed on living tissues of animals. The compounds, which control both bloodsucking parasites and flesh-eating parasites, are characterized by a 2-fluoroalkyl substituent, a single nitro substituent on the benzene ring, and a single fluoroalkyl or chloro substituent on the benzene ring.

16 Claims, No Drawings

CONTROL OF ANIMAL PARASITES WITH BENZIMIDAZOLES

CROSS-REFERENCE

This application is a continuation-in-part of my co-pending application Ser. No. 528,606, filed Dec. 2, 1974, now abandoned was a continuation-in-part of my then co-pending application Ser. No. 450,128, filed Mar. 11, 1974, now abandoned.

BACKGROUND OF THE INVENTION

The control of animal parasites is one of the oldest and most important problems of the animal husbandry industry. Many types of parasites afflict virtually all species of animals. Most animals are afflicated by free-flying parasites such as flies, crawling ectoparasites such as lice and mites, burrowing parasites such as bots and grubs, and by microscopic endoparasites such as coccidia, as well as by larger endoparasites such as worms. Thus, the control of parasites even in a single host species is a complex and many-sided problem.

The insect and acarina parasites which consume living tissues of a host animal are particularly harmful. The group includes parasites of all the economic animals, including ruminant and monogastric mammals and poultry, and of companion animals such as dogs as well.

Many methods of control of such parasites have been tried. The screwworm has been practically eradicated in Florida by the release of great numbers of sterile male blowflies. The method obviously is applicable only to an easily isolated area. The free-flying insects are usually controlled by routine methods such as air-dispersed and contact insecticides and fly traps. The skin-inhabiting crawling parasites are usually controlled by dipping, drenching, or spraying the animals with appropriate parasiticides.

Some progress has been made in the systemic control of some parasites, particularly those which burrow in or migrate through the host animal. Systemic control of animal parasites is accomplished by absorbing a parasiticide in the bloodstream or other tissues of the host animal. Parasites which eat or come into contact with the parasiticide-containing tissue are killed, either by ingestion or contact. A few phosphate, phophoramidate, and phosphorothioate insecticides and acaricides have been found to be sufficiently nontoxic to be used systemically in animals.

Recently, the field of benzimidazole chemistry has been extremely active. A great many patents and publications have appeared disclosing a variety of substituted benzimidazoles, some of which have insecticidal and acaricidal activity.

For example, Belgian Pat. No. 766,870, Derwent Index No. 72165S-C, teaches a group of acaricidal benzimidazoles characterized by 1-carboxylate and 2-chlorofluoroalkyl substituents and a variety of substituents, including halo, nitro, and trifluoromethyl, on the benzene ring.

Newbold et al., U.S. Pat. No. 3,542,923, discloses an insecticidal method making use of benzimidazoles having no 1-substituent or a 1-carboxylate substituent, a 2-perfluoroalkyl substituent, and as many as four benzene ring substituents chosen from among a large group of substituents including nitro, halo, alkyl, carboxy, and so forth.

British Pat. No. 1,122,988 teaches insecticidal and acaricidal benzimidazoles of structures notable for the extremely wide variety of the benzene ring substituents, of which the compounds can have as many as four. The 2-substituents of the components are perfluoroalkyl, and the 1-substituent, if present, is alkyl or aryl.

British Pat. Nos. 1,087,561 and 1,144,620 provide further disclosure of insecticidal 2-perfluoroalkyl benzimedazoles.

French Pat. No. 1,430,139 adds another group of insecticidal, acaricidal, and nematocidal benzimidazoles bearing as many as four benzene ring substituents chosen from the group including nitro, chloro, and cyano, among others, and a 2-haloalkyl substituent.

British Pat. No. 1,113,999 discloses a group of 1-thiocarbamoylbenzimidazoles which are insecticides active against pests such as mustard beetles, aphids, and mosquitoes.

South African Pat. No. 69.02813 teaches the biological activity of a family of benzimidazoles including compounds with 1-carboxylate and 1-sulfonyl substituents. The compounds are insecticides and acaricides.

Holan et al., U.S. Pat. No. 3,448,115, discloses a family of substituted benzimidazoles characterized by a 2-dichlorofluoromethyl or chlorodifluoromethyl substituent. The compounds of the patent are stated to be anthelmintics and herbicides.

Hannah et al., U.S. Pat. No. 3,749,734, discloses a group of 1-cyanobenzimidazoles having chlorine atoms on the phenyl ring which are said to be anthelmintics and ectoparasiticides.

SUMMARY

This invention provides to the art a new method of killing by ingestion insect and acarina parasites which comsume living tissues of a host animal which comprises orally or percutaneously administering to the host animal a parasiticidally-effective amount of a compound of the formula

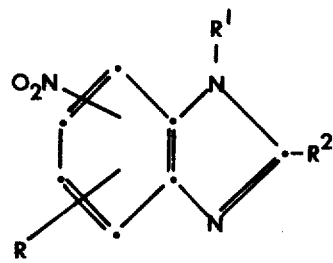

wherein R represents
chloro,
trifluoromethyl,
difluoromethyl, or
chlorodifluoromethyl;
$R^1$ represents
hydrogen,
hydroxy,

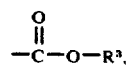

-continued

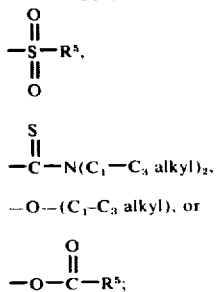

R² represents
chlorodifluoromethyl,
trifluoromethyl,
1,1,2,2-tetrafluoroethyl,
pentafluoroethyl,
heptafluoropropyl, or
heptafluoroisopropyl;

R³ represents
$C_1$–$C_6$ alkyl,
$C_2$–$C_3$ alkenyl,
phenyl, or
benzyl;

R⁴ represents
$C_1$–$C_5$ alkyl,
phenyl,
chlorophenyl,
anisyl, or
tolyl;

R⁵ represents
$C_1$–$C_3$ alkyl, or
phenyl;

or the ammonium, alkali metal, or alkaline earth metal salts of the above compounds wherein R¹ represents hydrogen.

DESCRIPTION OF THE PREFERRED EMBODIMENT

A preferred group of compounds which are particularly useful in my method have the formula

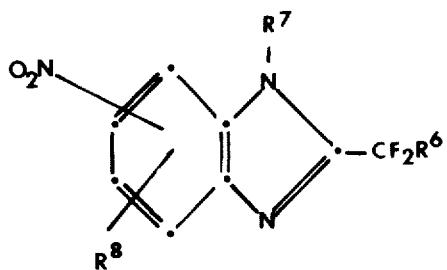

wherein R⁶ represents chloro, fluoro, difluoromethyl, or trifluoromethyl; R⁷ represents hydrogen, hydroxy, phenylsulfonyl, phenoxycarbonyl, $C_1$–$C_4$ alkoxycarbonyl, $C_1$–$C_3$ alkoxy, or

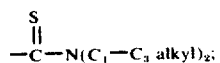

R⁸ represents chloro or trifluoromethyl.

The general chemical terms in the above generic formulae are used in the sense in which they are usually understood in organic chemistry. The following specific examples of substituents referred to by the general chemical terms are presented to assure clarity.

Alkali metal refers to atoms such as sodium, potassium, and lithium.

Alkaline earth metal refers to atoms such as calcium, magnesium, and strontium.

$C_1$–$C_3$ alkyl, $C_1$–$C_6$ alkyl, $C_1$–$C_4$ alkyl, $C_2$–$C_3$ alkenyl, $C_1$–$C_3$ alkoxy, and $C_1$–$C_5$ alkyl refer to substituents such as methyl, ethyl, isopropyl, isobutyl, hexyl, 2-pentyl, vinyl, allyl, t-butyl, methoxy, propoxy, and 3-hexyl.

The following specific compounds are presented to assure that those skilled in the organic chemical and parasitological arts understand the scope of my invention.

2-chlorodifluoromethyl-4-nitro-6-trifluoromethylbenzimidazole
6-nitro-2,4-bis(trifluoromethyl)benzimidazole
1-benzoyloxy-4-nitro-2,6-bis(trifluoromethyl)-benzimidazole
5-nitro-2,6-bis(trifluoromethyl)benzimidazole
4-nitro-2-pentafluoroethyl-6-trifluoromethylbenzimidazole
1-ethoxy-4-nitro-2,6-bis(trifluoromethyl)benzimidazole
4-nitro-2,6-bis(trifluoromethyl)benzimidazole
6-difluoromethyl-4-nitro-2-trifluoromethylbenzimidazole
allyl 4-nitro-2,6-bis(trifluoromethyl)-1 benzimidazolecarboxylate
4-nitro-N,N-dipropyl-2,6-bis(trifluoromethyl)-thio-1-benzimidazolecarboxamide
7-nitro-N,N-dipropyl-2,5-bis(trifluoromethyl)-thio-1-benzimidazolecarboxamide
ethyl 4-nitro-2,6-bis(trifluoromethyl)-1-benzimidazolecarboxylate
phenyl 4-nitro-2,6-bis(trifluoromethyl)-1-benzimidazolecarboxylate
N,N-diethyl-4-nitro-2,6-bis(trifluoromethyl)thio-1-benzimindazolecarboxamide
1-acetyl-7-nitro-2,5-bis(trifluoromethyl)benzimidzole
2,6-bis(trifluoromethyl)-4-nitro-1-phenylsulfonyl-benzimidazole
1-(p-anisoyl)-4-nitro-2,6-bis(trifluoromethyl)-benzimidazole
1-methoxy-4-nitro-2,6-bis(trifluoromethyl)benzimidazole
2,6-bis(trifluoromethyl)-4-nitrobenzimidazole, sodium salt
n-hexyl 4-nitro-2,6-bis(trifluoromethyl)-1-benzimidazolecarboxylate
isopropyl 4-nitro-2,6-bis(trifluoromethyl)benzimidazole
1-benzoyl-4-nitro-2,6-bis(trifluoromethyl)benzimidazole
1-(4-chlorobenzoyl)-4-nitro-2,6-bis(trifluoromethyl-benzimidazole
N,N-dimethyl-4nitro-2,6-bis(trifluoromethyl)thio-1benzimidazolecarboxamide
N,N-7-nitro-2,5-bis(trifluoromethyl)thio-1-benzimidazolecarboxamide
benzyl 2,6-bis(trifluoromethyl)-4-nitro-1-benzimidazolecarboxylate
benzyl 2,5-bis(trifluoromethyl)-7-nitro-1-benzimidazolecarboxylate methyl 4-nitro-2,6-bis(trifluoromethyl)-1-benzimidazolecarboxylate methyl 7-nitro-2,5-bis(trifluoromethyl)-1-benzimidazolecarboxylate isopropyl 2-chlorodifluoromethyl-4-nitro-6-trifluoromethyl-1-benzimidazolecarboxylate 1-acetyl-4-nitro-2,6bis(trifluoromethyl)benzimidazole 1hexanoyl-4-nitro-2,6bis(trifluoromethyl)-benzimidazole 7-nitro-2(1,1,2,2-tetrafluoroethyl)-5-trifluoromethylbenzimidazole 1-ethoxy-4-nitro-2-pentafluoroethyl-6-trifluoromethylbenzimidazole phenyl 2-chlorodifluoromethyl-4-nitro-6-trifluoromethyl-1-benzimidazolecarboxylate 5-chloro-6-nitro-2-trifluoromethylbenzimidazole
6-chloro-2-trifluoromethyl-4-nitrobenzimidazole
4-chloro-5-nitro-2-trifluoromethylbenzimidazole
1-hexanoyl-7-nitro-2,5-bis(trifluoromethyl)-benzimidazole 4-chloro-7-nitro-2-trifluoromethylbenzimidazole
4-chloro-6-nitro-2-trifluoromethylbenzimidazole
5-chloro-4-nitro-2-trifluoromethylbenzimidazole
5-chloro-2-heptafluoropropyl-7-nitrobenzimidazole
4-chlorodifluoromethyl-6-nitro-2-trifluoromethylbenzimidazole 5-nitro-2,6-bis(trifluoromethyl)benzimidazole, potassium salt 7-nitro-2,5-bis(trifluoromethyl)benzimidazole; calcium salt 6-difluoromethyl-4-nitro-1-propoxy-2-trifluoromethylbenzimidazole 4-chloro-6-nitro-2-trifluoromethyl-1-(p-xyloyl)-benzimidazole 1-acetoxy-4-nitro-2,6-bis(trifluoromethyl)benzimidazole 6-chloro-2-heptafluoroisopropyl-1-butyryloxybenzimidazole 1-methylsulfonyl-4-nitro-2,6-bis(trifluoromethyl)-benzimidazole 1-propylsulfonyl-7-nitro-2,5-bis(trifluoromethyl)-benzimidazole 1-butyryl-7-nitro-2,5-bis(trifluoromethyl)benzimidazole 5-chloro-1-hydroxy-7-nitro-2-trifluoromethylbenzimidazole 2-chlorodifluoromethyl-1-hydroxy-4-nitro-6-trifluoromethylbenzimidazole 6-chloro-1-hydroxy-4-nitro-2-(1,1,2,2-tetrafluoroethyl)benzimidazole 7-difluoromethyl-1-hydroxy-5-nitro-2-pentafluoroethylbenzimidazole 6-chlorodifluoromethyl-2-heptafluoropropyl-1-hydroxy-4-nitrobenzimidazole 2-heptafluoroisopropyl-1-hydroxy-6-nitro-5-trifluoromethylbenzimidazole The preferred compounds of my invention are the following.

phenyl 4-nitro-2,6-bis(trifluoromethyl)-1-benzimidazolecarboxylate isopropyl 4-nitro-2,6-bis(trifluoromethyl)-1-benzimidazolecarboxylate 2-chlorodifluoromethyl-4-nitro-6-trifluoromethylbenzimidazole 1-ethoxy-4-nitro-2-pentafluoroethyl-6-trifluoromethylbenzimidazole phenyl 2-chlorodifluoromethyl-4-nitro-6-trifluoromethyl-1-benzimidazolecarboxylate ethyl 2-chlorodifluoromethyl-4-nitro-6-trifluoromethyl-1-benzimidazolecarboxylate isopropyl 4-nitro-2-(1,1,2,2-tetrafluoroethyl)-6-trifluoromethyl-1-benzimidazolecarboxylate 4-nitro-2-(1,1,2,2-tetrafluoromethyl)-6-trifluoromethylbenzimidazole 2-chlorodifluoromethyl-4-nitro-6-trifluoromethylbenzimidazole 1-methoxy-4-nitro-2-(1,1,2,2-tetrafluoroethyl)-6-trifluoromethylbenzimidazole 1-hydroxy-4-nitro-2-(1,1,2,2-tetrafluoroethyl)-6-trifluoromethylbenzimidazole Organic chemists are now aware of the synthetic methods which are used to make the benzimidazoles of my method. Some explanation of the synthetic methods and a few specific examples will be given, however, to assure that all may obtain the compounds.

The method of synthesis depends on the 1-substituent of the benzimidazole to be made. The synthesis of all the benzimidazoles except the 1-hydroxy, 1-alkoxy and 1-acyloxy-substituted compounds begins with the reaction of an appropriately substituted o-phenylenediamine with a fluoroalkanoic acid. The reaction can be done in 5N acid, such as HC1, at reflux temperature. The 2-substituent of the benzimidazole to be synthesized comes from the substituents of the alkanoic acid. For example, if a 2-trifluoromethylbenzimidazole is to be made, the phenylenediamine is reacted with trifluoroacetic acid. If the benzimidazole is to have a 2-heptafluoropropyl substituent, the reactant is heptafluorobutyric acid.

Higher yields of the benzimidazoles are obtained by reacting the o-phenylenediamine with the fluoroalkanoic acid in the presence of halide such as phosphorus oxychloride or phosphorus pentachloride in a solvent such as pyridine. It is also possible to perform the synthesis in the presence of an acid chloride formed in situ in the reaction mixture. The reaction goes quickly at reflux temperature.

The benzene ring substituents of the benzimidazole are the ring substituents of the o-phenylenediamine. For example, if the benzimidazole is to have a 4-chloro-6-nitro substitution, the reactant is 3-chloro-5-nitro-o-phenylenediamine. If the benzimidazole is to be a 7-nitro-5-chlorodifluoromethyl compound, the reactant is 6-nitro-4-chlorodifluoromethyl-o-phenylenediamine.

The 1-substituents of the benzimidazoles, other than 1-hydroxy, 1-alkoxy and 1-acyloxy, are conveniently made by the direct attachment of the desired 1-substituent to the benzimidazole. The sulfonyl, carboxylate, thiocarbamoyl, and acyl substituents are attached to the 1-position of the benzimidazole ring system by direct reaction of the benzimidazole with a halide derivative of the desired substituent. For example, an ethylsulfonyl is provided by reaction with ethylsulfonyl chloride; a propylcarboxylate, by reaction with propyl chloroformate; an anisoyl substituent, by reaction with anisoyl chloride; and an N,N-diethylthicarbamoyl substituent, by reaction with N,N-diethylthiocarbamoyl bromide. The reaction goes easily at room temperature in solvents such as acetonitrile, tetrahydrofuran, and benzene. Either the benzimidazole itself or an alkali metal salt of it may be used as the starting compound for the reaction. Examples 2–4 below illustrate the synthesis.

The benzimidazoles with 1-alkoxy and 1-acyloxy substituents are prepared through a 1-hydroxybenzimidazole, which is prepared by reductive ring closure of an appropriately substituted acetanilide which is prepared in turn from an o-nitroaniline.

A 1-alkoxy-substituted benzimidazole is easily made by reacting the 1-hydroxybenzimidazole with an alkyl halide in the presence of an alkali metal alkoxide, hydroxide, or carbonate at ambient or elevated temperature. A 1-acyloxybenzimidazole is synthesized at room temperature by reaction of a 1-hydroxybenzimidazole with an acyl chloride. For example, a 1-benzoyloxybenzimidazole is made with benzoyl chloride as the reactant, carrying out the reaction at room temperature in pyridine.

Alakli metal, alkaline earth metal, and ammonium salts of the 1-unsubstituted benzimidazoles are easily made by the common methods. For example, alkali metal and alkaline earth metal salts are made by reaction of a benzimidazole with a methoxide of the metal in methanol at room temperature. Such salts are also conveniently prepared from hydroxides of the alkali and alkaline earth metals by dissolving the hydroxide in an appropriate solvent such as water, aqueous alcohol, or aqueous acetone, and adding the benzimidazole compound to the solution at room temperature. Ammonium salts are prepared by contacting a benzimidazole with ammonium hydroxide or by bubbling ammonia gas through a solution of the benzimidazole.

The examples immediately below show the synthesis of typical exemplary compounds. Organic chemists, guided by the above general teaching as well as the common skill of the chemical art, can use the methods of the examples below to prepare all the benzimidazoles useful in my method.

The first example illustrates the synthesis of an intermediate o-phenylenediamine, as well as the synthesis of a typical benzimidazole.

EXAMPLE 1

4-nitro-2-pentafluoroethyl-6-trifluoromethylbenzimidazole

A solution of 40.5 g. of 2,6-dinitro-4-trifluoromethyl-1-chlorobenzene in 300 ml. of benzene was mixed with 250 ml. of 14N ammonium hydroxide. The mixture was stirred at room temperature for about 1½ hours, when another 100 ml. of 14N ammonium hydroxide was added. The mixture was stirred for 2 hours more. The mixture was allowed to separate in layers, and the organic layer was separated, washed with water, and dried. Evaporation of the solvents under vacuum gave 2,6-dinitro-4-trifluoromethylaniline, m.p. 142°–144°C. after recrystallization from hexane-benzene.

A 24 g. portion of the above product was dissolved in 300 ml. of ethanol. The solution was heated to about 35°C. and 110 ml. of 20 percent aqueous ammonium polysulfide, containing 5 percent free sulfur, was added. The temperature of the mixture rose spontaneously to about 60°C., at which temperature it was maintained for about 10 minutes. The reaction mixture was then cooled to about 40°C. and poured into water. The resulting mixture was filtered. Acetone was added to the precipitate to remove residual product from the sulfur, and the resulting suspension was filtered also. Excess benzene was added to the combined filtrates, and the liquid mixture was then evaporated to dryness. Recrystallization of the dry solid produced 3-nitro-5-trifluoromethyl-o-phenylenediamine, m.p. 121°–123°C.

A 44 g. portion of the above intermediate product was mixed with 100 ml. of pyridine and 35 g. of pentafluoropropionic acid. The mixture was stirred while 65 g. of phosphorus oxychloride was added dropwise. The mixture was then heated at reflux temperature for 5 minutes and cooled. When the temperature of the mixture had decreased to about 70°C., 300 ml. of water was added, and the mixture was vigorously stirred while it was cooled to room temperature. A light brown solid precipitated which was separated by filtration and air-dried. The product was 59 g. of 4-nitro-2-pentafluoroethyl-6-trifluoromethylbenzimidazole, m.p. 124°–125°C.

The following synthetic examples illustrate the synthesis of 1-substituted benzimidazoles.

EXAMPLE 2

4-nitro-1-phenylsulfonyl-2,6-bis(trifluoromethyl)benzimidazole

A solution of 3.5 g. of phenylsulfonyl chloride in 20 m. of anhydrous acetonitrile was added to a solution of 6.4 g. of 4-nitro-2,6-bis(trifluoromethyl)benzimidazole, sodium salt in 50 ml. of anhydrous acetonitrile. The mixture was stirred at room temperature for 2 hours, and the reaction mixture was filtered. The filtrate was evaporated to dryness under vacuum, and the residue was recrystallized from benzenepentane to yield 4-nitro-1-phenylsulfonyl-2,6-bis(trifluoromethyl)benzimidazole, m.p. 183°–185°C.

EXAMPLE 3 phenyl 4-nitro-2,6-bis(trifluoromethyl)-1-benzimidazolecarboxylate

The procedure of Example 2 was repeated, using phenylchloroformate in place of phenylsulfonyl chloride. The product was isolated by the procedure of Example 2 and recrystallized from pentane to yield phenyl 4-nitro-2,6-bis-(trifluoromethyl)-1-benzimidazolecarboxylate, m.p. 100°–103°C.

The method of Example 2 is also used, substituting an N,N-dialkylthiocarbamoyl chloride for the sulfonyl chloride, in the synthesis of my 1-thiocarbamoyl-substituted compounds.

The 1-acylbenzimidazoles are easily synthesized by a method exemplified by the following.

EXAMPLE 4

1-acetyl-2,6(2,5)-bis(trifluoromethyl)-4(7)-nitrobenzimidazole

A 9 g. portion of 4-nitro-2,6-bis(trifluoromethyl)-benzimidazole was dissolved in about 600 ml. of dry benzene, and 3.3 g. of triethylamine was added. To the solution was added dropwise 2.5 g. of acetyl chloride dissolved in 75 ml. of benzene. The addition was over a period of about 2.5 hours. The mixture was then stirred overnight at room temperature. In the morning, the reaction mixture was filtered, and the filtrate was evaporated under vacuum to give a yellow-orange solid residue, m.p. 100°–114°C. Recrystallization of the residue from benzene gave a product in the form of gummy platelets, m.p. 115°–125°C. Nuclear magnetic resonance analysis of the product indicated a 50–50 mixture of the two acetyl isomers, 1-acetyl-2,5-bis(trifluoromethyl)-7-nitrobenzimidazole and 1-acetyl-2,6-bis(trifluoromethyl)-4-nitrobenzimidazole, which were separated by column chromatography.

Benzimidazoles which have 1-alkoxy and 1-acyloxy substituents are prepared through a 1-hydroxybenzimidazole. The example below illustrates the synthesis of 1-hydroxybenzimidazoles.

EXAMPLES 5

1-hydroxy-4-nitro-2,6-bis(trifluoromethyl)benzimidazole

A solution of 25.1 g. of 2,6-dinitro-4-trifluoromethylaniline in 100 ml. of pyridine was treated with trifluoroacetyl chloride, which has been prepared from 10 ml. of trifluoroacetic acid. Ethanol was added to the resulting mixture until it was homogeneous, and the reaction mixture was then evaporated under vacuum. The residue after evaporation was washed with water, dried, dissolved in acetone, and filtered. Chloroform was added to the filtrate until the product precipitated. The precipitate was separated by filtration and dried to obtain the purified intermediate, 2',6'-dinitro-4'-trifluoromethyl-2,2,2-trifluoroacetanilide.

A 1.75 g. portion of the above intermediate was dissolved in 100 ml. of ethyl acetate. One hundred mg. of 5 percent palladium on carbon was added, and the mixture was hydrogenated at an initial pressure of 13 psig. and room temperature until 0.01 mole of hydrogen had been taken up. The reaction mixture was then filtered and evaporated to dryness. The solid residue was taken up in about 300 ml. of ether, extracted into 5 percent $Na_2CO_3$, and acidified. The desired 1-hydroxy-4-nitro-2,6-bis(trifluoromethyl)benzimidazole precipitated and was separated by filtration. The product was then taken up in ether and dried over $MgSO_4$, and the ether was evaporated. The product was crystalized from chloroform to produce 900 mg. of 1-hydroxy-4-nitro-2,6-bis-(trifluoromethyl)benzimidazole, m.p. 222°–224°C.

The 1-alkoxy compounds are made from 1-hydroxy compounds as shown in the following example.

EXAMPLE 6

1-ethoxy-4-nitro-2,6-bis(trifluoromethyl)benzimidazole

A 6 g. portion of 1-hydroxy-4-nitro-2,6-bis(trifluoromethyl)benzimidazole was mixed with 50 ml. of methanol, 10 ml. of ethyl iodide, and 2.5 g. of sodium ethoxide. The mixture was heated at reflux temperature overnight with stirring, and was then cooled and evaporated to dryness. The residue was taken up in ether, and the ether solution was washed with water. The ether layer was then evaporated to dryness, and the residue was recrystallized from petroleum ether to produce the desired 1-ethoxy-4-nitro-2,6-bis(trifluoromethyl)benzimidazole, m.p. 94°–96°C.

Similarly, the 1-acyloxy compounds are readily synthesized by reacting the appropriate 1-hydroxybenzimidazole with an acyl chloride. For example, 1-benzoyloxy-4-nitro-2,6-bis(trifluoromethyl)benzimidazole is made by reacting 1-hydroxy-4-nitro-2,6-bis(trifluoromethyl)benzimidazole with benzoyl chloride at room temperature in pyridine.

The example below illustrates the synthesis of benzimidazole salts.

EXAMPLE 7

4-nitro-2,6-bis(trifluoromethyl)benzimidazole, sodium salt

A mixture of 6 g. of 4-nitro-2,6-bis(trifluoromethyl)benzimidazole and 1.1 g. of sodium methoxide in 100 ml. of methanol was prepared. The reaction mixture was shaken for a few minutes at room temperature and filtered. Evaporation of the filtrate to dryness under vacuum produced the sodium salt of 4-nitro-2,6-bis(trifluoromethyl)-benzimidazole, m.p. about 200°C.

The method of parasite control which I have invented is of the systemic type. The benzimidazole compounds described above have the ability to permeate the living tissues of a host animal to which one of the compounds is administered. Insect and acarina parasites which consume blood or other living tissues of the host animal ingest the compounds with which the tissue is permeated, and are thereby killed. It is probable that the blood is the agency through which the compound is dispersed through the host animal, but parasites such as screwworms, which do not suck blood, are killed by my method, indicating that the compounds permeate other tissues as well as blood.

Some parasites, such as most ticks, feed on living tissues of the host animal during most of the parasite's life. Other parasites, such as screwworms, feed on the host only in the larval stage. A third group of parasites, such as the bloodsucking flies, feed on animal hosts only in the adult stage. Administration of the benzimidazoles of my method to host animals kills parasites which feed on the living tissues of the animals, no matter what the life stage of the feeding parasite.

All the species of insect and acarina parasites which feed on the living tissues of animals are killed by my method. The parasites which suck the host animal's blood, those which burrow into and feed on the animal's tissue, and those, like the larvae of the bot flies, which enter a natural orifice of the host, attach to the mucous membranes, and feed therefrom are all equally effectively killed. For the sake of clarity, a number of specific parasites of various host animals which are controlled by my method will be mentioned. The parasitic life stage and the means by which it infests the host animal are given for each parasite.

Parasites of Horses
  horsefly, adult, bloodsucking
  stable fly, adult, bloodsucking
  black fly, adult, bloodsucking
  horse sucking louse, immature, adult, bloodsucking
  mange mite, nymph, adult, skin-burrowing
  scab mite, adult, skin-eating
  common horse bot fly, larva, migrating in alimentary canal
  chin fly, larva, migrating in alimentary canal
  nose bot fly, larva, migrating in alimentary canal
Parasites of Bovines
  horn fly, adult, bloodsucking
  cattle biting louse, adult, skin-eating
  cattle bloodsucking louse, nymph, adult, bloodsucking
  tsetse fly, adult, bloodsucking
  stable fly, adult, bloodsucking
  horse fly, adult, bloodsucking
  cattle follicle mite, adult, skin-burrowing
  cattle tick, larva, nymph, adult, bloodsucking
  ear tick, nymph, bloodsucking Gulf Coast tick, adult, bloodsucking
Rocky Mountain spotted-fever tick, adult, bloodsucking
  lone star tick, adult, bloodsucking
  heel fly, larva, migrating through the body
  bomb fly, larva, migrating through the body
  blowfly, larva, infesting wounds
  assassin bug, adult, bloodsucking
Parasites of Swine
  hog louse, nymph, adult, bloodsucking
  chigoe flea, adult, bloodsucking
Parasites of Sheep and Goats
  bloodsucking body louse, adult, bloodsucking
  bloodsucking foot louse, adult, bloodsucking
  sheep ked, adult, bloodsucking
  sheep scab mite, nymph, adult, skin-eating
  nose fly, larva, migrating in the sinuses
  greenbottle fly, larva, infesting wounds
  black blowfly, larva, infesting wounds
  secondary screwworm, larva, infesting wounds
Parasites of Poultry
  bed bug, nymph, adult, bloodsucking
  Southern chicken flea, adult, bloodsucking
  fowl tick, nymph, adult, bloodsucking
  chicken mite, nymph, adult, bloodsucking
  scaly-leg mite, adult, skin-burrowing
  depluming mite, adult, skin-burrowing
Parasites of Dogs
  horse fly, adult, bloodsucking
  stable fly, adult, bloodsucking
  mange mite, nymph, adult, skin-burrowing
  dog follicle mite, adult, burrowing in hair follicles
  flea, adult, bloodsucking It will be understood that the parasites mentioned above are not confined to the single host animal with which each is here identified. Most parasites inhabit various hosts, although each parasite has a favorite host. For example, the mange mite attacts at least horses, hogs, mules, humans, dogs, cats, foxes, rabbits, sheep, and cattle. Horseflies freely attack horses, mules, cattle, hogs, dogs, and most other animals. My method effectively kills parasites of the types described above growing in the host animals mentioned above, and in other host animals as well. For example, my invention is effective in cats, camels, and zoo animals.

The host animals in which my method is preferably practiced are dogs, bovines, sheep, or horses. The method is preferably used for the control of ticks, fleas, flies, or screwworms.

The time, manner, and rates at which the compounds of my method are effectively administered may be varied over a wide range. Detailed explanation of the ways in which my method is practiced will be given.

The compounds are administered to the animals at rates from about 1 to about 100 mg./kg. The best rate for killing a given parasite infesting a given animal must be determined individually, but it will be found that in most cases the optimum rate is within the preferred range of from about 2.5 to about 50 mg./kg. The optimum rate for a given instance depends on such factors as the health of the animal to be treated, the susceptibility of the parasite of primary concern, the expense which can be borne by the animal, and the degree of control desired. Lower rates are safer for the host animal, less expensive, and often easier to administer, but are likely to give incomplete or minimum control of the parasite so that reinfestation may occur. On the other hand, higher rates of administration give more complete control of the parasites, but are more expensive and may impose a stress on the treated animals.

The compounds of my method are effective when administered at any time of year to animals of any age. It is possible to administer the compounds of my method to the animals continuously, as by constant feeding of a diet which contains one of the compounds, and thus assure that all parasites which contact the treated animals will be killed. Such administration is by no means economical, and it will usually be found best to administer the compounds at such times as to give the best return of parasite control for the compound expended. Certain parasites, such as cattle grubs, which are the larvae of the heel fly and the bomb fly, have a known active season when they attack animals. If such a parasite is of primary importance, my method can be practiced only during that season with assurance of year-round control of the parasite. Other parasites, such as ticks, infest and bite animals essentially the year round. Control of such parasites can still be accomplished with relatively brief periods of administration by administering the compound to all the animals on a farm or in an area for a short period of time, such as for a few weeks. All the parasites of a generation are thus killed, and the animals can be expected to remain parasite-free for a considerable length of time, until reinfested by parasites arriving with imported animals or the like.

The compounds of my method may be administered by any of the usual oral and percutaneous routes. It should be noted that many of the compounds of my method are chemically changed by passage through the rumen of a ruminant animal. Oral administration to ruminant animals is therefore advisable only if the compounds are protected from the rumen environment by a special formulation. Such formulations will be discussed below.

The formulation and administration to animals of biologically-effective compounds is a very old and developed art. Some explanation of the different formulations and methods of administration will be given to enable all to practice my method of parasite control.

Percutaneous administration of the benzimidazole compounds is carried out in the ways usual in the animal veterinary art. It is convenient to use a water-soluble salt of the benzimidazole, so that no elaborate formulation is required. On the other hand, if a water-insoluble benzimidazole is desired, it is practical to dissolve the compound in a physiologically-acceptable solvent, such as the polyethylene glycols for example. It is likewise practical to formulate an injectable suspension of the benzimidazole as a fine powder, suspended in a formulation of physiologically-acceptable nonsolvents, surfactants, and suspending agents.

The nonsolvent can be, for example, a vegetable oil such as peanut oil, corn oil or sesame oil, a glycol such as a polyethylene glycol, or water, depending on the benzimidazole chosen.

Suitable physiologically-acceptable adjuvants are necessary to keep the benzimidazole suspended. The adjuvants can be chosen from among the emulsifiers, such as salts of dodecylbenzene sulfate and toluenesulfonate, ethylene oxide adducts of alkylphenol, and oleate and laurate esters, and from the dispersing agents such as salts of naphthalenesulfonate, lignin sulfonate and fatty alcohol sulfates. Thickeners such as carboxymethyl cellulose, polyvinylpyrrolidone, gelatin and the alginates are also used as adjuvants for injectable suspensions. Many classes of surfactants, as well as those which have been discussed above, serve to suspend the benzimidazoles. For example, lecithin and the polyoxyethylene sorbitan esters are useful surfactants.

Percutaneous administration is conveniently accomplished by subcutaneous, intramuscular, and even intravenous injection of the injectable formulation. Conventional needle-type injection devices as well as needle-less air-blast injection devices are useful.

It is possible to delay or sustain the permeation of the benzimidazole compound through the animal's living tissues by proper formulation. For example, a very insoluble benzimidazole may be used. In that event, the slight solubility of the compound causes sustained action because the body fluids of the animal can dissolve only a small amount of the compound at any one time.

Sustained action of the benzimidazole can also be obtained by formulating the compound in a matrix which will physically inhibit dissolution. The formulated matrix is injected into the body where it remains as a depot from which the compound slowly dissolves. Matrix formulations, now well known in the art, are formulated in waxy semisolids such as vegetable waxes and high molecular weight polyethylene glycols.

Even more effective sustained action is obtained by introducing into the animal an implant containing one of the compounds. Such implants are now well known in veterinary medicine, and are usually made of a silicone-containing rubber. The benzimidazole compound is dispersed through a solid rubber implant or is contained inside a hollow inplant. Care must be taken to choose a benzimidazole compound which is soluble in the rubber from which the implant is made, since it is dispersed by first dissolving in the rubber, and then leaching out of the rubber into the body fluids of the treated animal.

The rate at which the compound is released from an implant, and hence the length of time during which the implant remains effective, is controlled with good accuracy by the proper adjustment of the concentration of the compound in the implant, the external area of the implant, and the formulation of the polymer from which the implant is made.

Administration of benzimidazole compounds by means of an implant is a particularly preferred method of my invention. Such administration is highly economical and efficacious, because a properly designed implant maintains a constant concentration of the compound in the tissues of the host animal. An implant can be designed to supply compound for several months, and is easily inserted in the animal. No further handling of the animal or concern over the benzimidazole dosage is necessary after the insertion of the implant.

Oral administration of a benzimidazole may be performed by mixing the compound in the animal's feed or drinking water, or by administering oral pharmaceutical dosage forms such as drenches, tablets, or capsules.

When a compound of my method is to be administered orally to a ruminant animal, it is necessary to protect the compound from the deleterious effect of the rumen processes. The veterinary pharmaceutical art is now aware of effective methods for coating and encapsulating drugs to protect them from the rumen. For example, coating materials and methods are disclosed in Grant et al., U.S. Pat. No. 3,697,640. Grant teaches a method of protecting substances from action of the rumen by coating the substances with a film of cellulose propionate 3-morpholinobutyrate. Such a film can be used to protect the benzimidazoles of my method. Conveniently, tablets, or capsules containing a benzimidazole are coated with the film in a coating pan or a fluidized bed spray apparatus. Pellets of the parasiticide may be made, coated with the film, and filled into capusles. Alternatively, a solid mixture of the benzimidazole and the film-forming agent may be made and broken or ground into small particles, each of which comprises the benzimidazole enclosed in a matrix of the film-forming agent. The particles may be filled into capsules for oral administration, or made into an oral suspension.

The formulation of veterinary drugs in animal feed is an extremely well-known art. It is usual to formulate the compound first as a premix in which the benzimidazole is dispersed in a liquid or particulate solid carrier. The premix may conveniently contain from about 1 to about 400 g. of drug per pound, depending on the desired concentration in the feed. As the art is aware, many benzimidazoles will be hydrolyzed or degraded by constituents of animal feed. Such compounds are routinely formulated in protective matrices such as gelatin and the like before addition to the premix. The premix is in turn formulated into feed by dispersing it in the feed mixture in a conventional mixer. The correct amount of benzimidazole, and hence of premix, to mix in the feed is easily computed by taking into account the weight of the animals, the approximate amount each animal eats per day, and the concentration of the benzimidazole in the premix.

Likewise, the amount of a benzimidazole compound to administer in the drinking water of animals is computed by taking into account the animal's weight and the amount each animal drinks per day. It is most convenient to use a water-soluble benzimidazole salt as a drinking water treatment. If such a salt is not desired, then a suspendable formulation of the desired benzimidazole must be made. The formulation may be a suspension in the concentrated form, which suspension is mixed into the drinking water, or may be a dry preparation which is mixed with and suspended in the drinking water. In either event, the benzimidazole must be in a finely-powdered form, and the formulation follows the same principles discussed above for injectable suspensions.

The compounds can easily be formulated into tablets and capsules according to the conventional methods, about which no teaching is required here. Drench formulations comprise the benzimidazole compound dissolved or dispersed in an aqueous liquid mixture. Again, it is most convenient to make the drench by dissolving a water-soluble benzimidazole salt. It is almost as convenient, however, and equally efficacious to use a dispersion of the compound made in the same way that the drinking water formulations discussed above are made.

The examples immediately below show the great effectiveness of my method in controlling a number of parasites which normally affect economic animals when those parasites were fed on guinea pigs to which the compounds of my method had been administered. The compounds were tested against screwworms, which are larvae of the black blowfly, against the stable fly, and against nymphs of the lone star tick. The blowfly and stable fly are insects; the lone star tick is representative of the acarina.

The stable fly is a common free-flying, bloodsucking parasite; the lone star tick is a typical bloodsucking parasite which spends the nymphal and part of the adult periods of the life cycle attached to the host animal, usually cattle. Blowfly larvae, or screwworms, hatch from eggs laid near a wound of the host animal by the free-flying insect. The larvae eat their way into the healthy flesh exposed by the wound and pass part of the life cycle therein, feeding on the host's flesh and blood.

The stable fly is parasitic on horses, mules, cattle, hogs, dogs, cats, sheep, goats, rabbits, and humans. The lone star tick is primarily a cattle parasite, but also attacks horses, mules, and sheep. Blowfly larvae attack any wounded animal, but are particularly harmful to cattle, hogs, horses, mules, sheep and goats.

The test animals were male guinea pigs weighing 400–500 g. The test compounds were administered to the animals at the rate of 10 mg./kg. Each compound was administered orally to one animal, and injected subcutaneously (SC) to another animal. The test compounds were administered as dispersions in sorbitan monolaurate. Each group of treated guinea pigs was tested along with two pigs to which a sorbitan monolaurate blank was administered.

Each guinea pig was infested with 25 nymphs of the lone star tick 48 hours before treatment. Twenty-four hours before treatment, each pig was wounded, and the wounds were infested with larvae of the black blowfly. At 4 hours, 24 hours, and in some cases at 48 hours after treatment, stable flies were fed on the guinea pigs.

The animals and the parasites with which they were infested were observed. The stable flies were observed 24 hours after they fed on the pigs and the number of flies killed by the blood they ingested was counted. The blowfly larvae were removed from the wounds 24 hours after treatment, and the number of dead larvae was counted. The ticks were observed during their engorgement period, and the number of them killed by the blood they sucked from the guinea pigs was counted also. The observations are reported below as the percent of each parasite which was killed.

| Compound Name | Route of Administration | Blowfly Larvae | Percent of Parasites Killed Stable flies 4 hours | Stable flies 24 hours | Tick Nymphs |
|---|---|---|---|---|---|
| Example 8 4-nitro-2-pentafluoroethyl-6-trifluoromethyl-benzimidazole | Oral | 90% | 76% | — | 100% |
| | SC | 0 | 0 | 7% | 100 |
| Example 9 7-nitro-2,5-bis-(trifluoromethyl)-benzimidazole | Oral | 100 | 50 | 32 | 100 |
| | SC | 0 | 0 | 20 | 100 |
| Example 10 phenyl 4-nitro-2,6-bis(trifluoromethyl)-1-benzimidazolecarboxylate | Oral | 100 | 65 | 21 | 100 |
| | SC | 100 | 0 | 25 | 100 |
| Example 11 2,6-bis(trifluoromethyl)-4-nitro-1-phenylsulfonyl-benzimidazole | Oral | 100 | 10 | 25 | 100 |
| | SC | 0 | 0 | 0 | 0 |
| Example 12 isopropyl 4-nitro-2,6-bis(trifluoromethyl)-1-benzimidazolecarboxylate | Oral | 100 | 51 | 7 | 100 |
| | SC | 0 | 0 | 0 | 75 |
| Example 13 N,N-dimethyl-7-nitro-2,5-bis-(trifluoromethyl)-thio-1-benzimidazolecarboxamide | Oral | 0 | 0 | 20 | 100 |
| | SC | 0 | 0 | 6 | 23 |
| Example 14 2-chlorodifluoromethyl-4-nitro-6-trifluoromethyl-benzimidazole | Oral | 100 | 73 | 91 | 100 |
| | SC | 100 | 0 | 32 | 100 |
| sorbitan monolaurate control | Oral | 0 | 10 | 8 | 0 |
| | SC | 0 | 5 | 0 | 8 |
| Example 15 6-chloro-2-trifluoromethyl-4-nitrobenzimidazole | Oral | 100 | 100 | 100 | 80 |
| | SC | 0 | — | — | 0 |
| Example 16 1-ethoxy-4-nitro-2-pentafluoroethyl-6-trifluoromethylbenzimidazole | Oral | 100 | 94 | 60 | 100 |
| | SC | 0 | 0 | 5 | 0 |
| Example 17 phenyl 2-chloro-difluoromethyl-4-nitro-6-trifluoro- | Oral | 100 | 94 | 87 | 100 |
| | SC | 100 | 53 | 83 | 88 |

-continued

| Compound Name | Route of Administration | Blowfly Larvae | Percent of Parasites Killed Stable flies 4 hours | Stable flies 24 hours | Tick Nymphs |
| --- | --- | --- | --- | --- | --- |
| methyl-1-benzimidazolecarboxylate | | | | | |
| sorbitan monolaurate control | Oral | 0 | 0 | 0 | 0 |
| | SC | 0 | 0 | 6 | 0 |
| Example 18 | | | | | |
| isopropyl 2-chloro-difluoromethyl-4-nitro-6-trifluoromethyl-1-benzimidazolecarboxylate | Oral | 100 | 77* | 96 | 100 |
| | SC | 100 | 92* | 92 | 100 |
| Example 19 | | | | | |
| benzyl 4-nitro-2-(1,1,2,2-tetrafluoro-ethyl)-6-trifluoro-methyl-1-benzimidazole-carboxylate | Oral | 100 | 28* | 38 | 100 |
| | SC | 0 | 4* | 25 | 100 |
| Example 20 | | | | | |
| isopropyl 4-nitro-2-(1,1,2,2-tetrafluoro-ethyl)-6-trifluoro-methyl-1-benzimidazole-carboxylate | Oral | 100 | 12* | 56 | 100 |
| | SC | 70 | — | — | 0 |
| Example 21 | | | | | |
| 1-methoxy-4-nitro-2-(1,1,2,2-tetrafluoro-ethyl)-6-trifluoro-methylbenzimidazole | Oral | 100 | 25* | 46 | 100 |
| | SC | 0 | 8* | 12 | 100 |
| sorbitan monolaurate control | Oral | 0 | 12* | 0 | 0 |
| | SC | 0 | 5* | 5 | 0 |

*Fed 48 hours after treatment

It is clear from the tests reported above that my method of animal parasite control is effective in controlling the different types of insect and acarina parasites which consume the host's living tissues. The tests, carried out in a standard laboratory animal, show the high potency of the benzimidazoles of my method in killing parasites which burrow into and consume the flesh of the host animal, which periodically suck blood of the animal, and which suck the host's blood while remaining affixed to the animal's skin. Both oral and percutaneous administration of the compounds to the animals controlled the parasites.

The examples below report tests of my parasiticidal method in dogs. The dogs used in the test were suffering from natural infestations of dog ticks and fleas. The compounds were administered intravenously or subcutaneously as aqueous dispersions.

It will be noted that, in most of the tests, the 48- and 72-hour data indicate that male ticks are killed more effectively than females. It is believed that the difference is due to the feeding habits of the sexes. Males feed more or less continuously, while females feed in periodic large meals. It is to be expected that the kill of female ticks will increase with time after the injection of the compound, as the compound moves through the host's body.

EXAMPLE 22

Two dogs were treated with 2.7 mg./kg. of isopropyl 4-nitro-2,6-bis(trifluoromethyl)-1-benzimidazolecarboxylate as a single intravenous injection. Twenty-four hours after administration of the compound, one of the dogs had died. The cause of death was not determined.

Both ticks and fleas on the surviving dog were visibly affected by the compound 24 hours after administration. Forty-eight hours after administration, it was found that 10 percent of the female ticks, 20 percent of the male ticks, and 95 percent of the fleas were dead.

EXAMPLE 23

Two other dogs were injected with 10 mg./kg. of ethyl 2-chlorodifluoromethyl-4-nitro-6-trifluoromethyl-1-benzimidazolecarboxylate as a single intravenous administration. When the animals were first observed, 24 hours after administration of the compound, there was no visible effect on the tick population, but the fleas were visibly injured.

The parasite population of the dogs was counted 48 hours after administration. At that time, 10 percent of the female ticks, 40 percent of the male ticks, and 100 percent of th fleas on both dogs were dead.

EXAMPLE 24

Four dogs were treated with 25 mg./kg. of isopropyl 4-nitro-2,6-bis(trifluoromethyl)-1-benzimidazolecarboxylate as a single subcutaneous injection. At the 24-hour observation, there was in general no effect on the parasites of the dogs, although the fleas on one dog were visibly affected.

At 48 hours, the flea populations on all the dogs were visibly reduced, and the ticks on two dogs were visibly injured by the compound.

The parasites remaining on the dogs were counted after 72 hours, and the percent killed was found to be as follows.

| Dog | Female Ticks | Male Ticks | Fleas |
| --- | --- | --- | --- |
| 1 | 20% | 80% | 100% |

-continued

| Dog | Female Ticks | Male Ticks | Fleas |
|---|---|---|---|
| 2 | 40 | 100 | 100 |
| 3 | 60 | 60 | 100 |
| 4 | 0 | 10 | 95 |

EXAMPLE 25

Another group of four dogs was injected with 50 mg./kg. of ethyl 2-chlorodifluoromethyl-4-nitro-6-trifluoromethyl-1-benzimidazolecarboxylate as a single subcutaneous injection. Neither the ticks nor the fleas were seen to be affected 24 hours after administration. The fleas on all the dogs were injected 48 hours after administration, as were the ticks on one dog.

The 72-hour parasite counts showed the following percent of kill.

| Dog | Female Ticks | Male Ticks | Fleas |
|---|---|---|---|
| 1 | 100% | 100% | 100% |
| 2 | 10 | 50 | 100 |
| 3 | 50 | 90 | 100 |
| 4 | 10 | 60 | 100 |

The examples above show the outstanding value of my method of parasite control. Single percutaneous injections of the compounds gave essentially complete control of fleas, and worthwhile control of ticks. The data indicate that, as the compounds continue to permeate through the tissues of the host, the tick kill will continue to improve.

The tests described in the following examples illustrate the efficacy of the method of this invention when carried out by percutaneous administration of the compounds to cattle. In most instances, the tests reported below were carried out on induced infestations of parasites.

EXAMPLE 26

A calf was treated with 5 mg./kg. of 4-nitro-2-(1,1,2,2-tetrafluoroethyl)-6-trifluoromethylbenzimidazole as a single subcutaneous injection. The compound was administered as a dispersion in sesame oil.

Adult stable flies were housed in chambers completely enclosed in wire screen. Two or more chambers, containing from 60 to 100 stable flies, were placed in contact with the clipped back of the calf 24 hours after administration of the compound. The flies were left to feed on the calf for 24 hours, after which the chambers were removed and replaced with a second set. The mortality of the flies was determined by counting the number of live and dead flies after each 24-hour exposure. Fresh flies were placed on the calf each day for as long as mortality was observed.

The mortality results were as follows:

| Days Post-Treatment | Stable Fly Mortality |
|---|---|
| 1 | 100% |
| 2 | 100 |
| 3 | 100 |
| 4 | 95 |
| 5 | 82 |
| 6 | 26 |
| 7 | 0 |

EXAMPLE 27

A calf was found to be infested with cattle tail lice. Fifteen of the lice were caught and placed in a testing chamber in order to obtain a critical measurement of the louse control obtained. the calf was treated exactly as described in Example 26, except that the lice were placed on the calf three hours after treatment.

Five hours after the parasites were placed on the calf, 12 of the 15 caged lice were dead, and all 15 of the lice were dead when observed 24 hours after administration of the compound.

Twenty-four hours after treatment, the calf was examined grossly, and was found to be visibly free of live tail lice.

EXAMPLE 28

A test was conducted against the nymph stage of the American dog tick. The test was conducted according to the procedure of Example 26, except that only one testing chamber containing 18 tick nymphs was used.

The chamber of nymphs was placed in contact with the clipped skin of the calf 24 hours after administration of the compound. The nymphs were examined 17 hours after they were placed on the calf, at which time all of them were dead. All of the dead nymphs were found to have had a blood meal.

EXAMPLE 29

The method of Example 26 was also used in a test against the assassin bug Rhodnius prolixus. In this instance, the testing chambers were left in contact with the treated calf for more than 24 hours, and were observed repeatedly at various times after being placed on the calf.

The following results were obtained with insects placed on the calf 24 hours after administration of the compound.

| Observation | Insect Mortality |
|---|---|
| 4 Hours | 25% |
| 22 Hours | 42 |
| 28 Hours | 58 |
| 48 Hours | 75 |

The following results were obtained with insects placed in contact with the calf 48 hours after the administration of the compound.

| Observation | Insect Mortality |
|---|---|
| 6 Hours | 27% |
| 24 Hours | 40 |
| 48 Hours | 53 |
| 72 Hours | 53 |

The following results were obtained when insects were placed in contact with the calf on the fifth day following compound administration.

| Observation | Insect Mortality |
|---|---|
| 18 Hours | 25% |
| 48 Hours | 30 |
| 72 Hours | 30 |

In all of the groups of insects used in this test, the insects which died tended to be the largest ones, over 12 mm. in length. Those which lived through the tests tended to be smaller and did not appear to have fed on blood during the test.

The tests reported immediately above demonstrate the long-lasting control of insect and acarina parasites which is obtained by the practice of the present invention. Administration of compounds of the invention, even at quite low rates, has been shown to kill such parasites which feed on the treated animals even several days after administration of the compound. It is also notable that the control obtained was very complete, in that all, or essentially all, of the parasites which fed on the animal were killed.

The following example reports representative results of a bio-assay test.

EXAMPLE 30

Larvae of the black blowfly were used as assay organisms in a bio-assay test system. The tests were carried out by administering a compound of this invention as a single subcutaneous injection to a calf. Samples of blood were withdrawn from the calf on successive days after the administration of the compound, and blowfly larvae were fed on the withdrawn whole blood. The end point of the test was recorded as the last day on which 90 percent or more of the blowfly larvae were killed.

Aqueous suspensions of 1-hydroxy-4-nitro-2-(1,1,2,2-tetrafluoroethyl)-6-trifluoromethylbenzimidazole were administered at rates of 5, 10 and 15 mg./kg. The 15 mg./kg. rate killed 90 percent or more of the larvae for four successive days, and administration at 10 mg./kg. killed the larvae for 3 days. The 5 mg./kg. rate was not effective.

Another compound, 2-chlorodifluoromethyl-4-nitro-6-trifluoromethylbenzimidazole, was administered to the calf at rates of 2.5, 5, 10 and 15 mg./kg. as sesame oil suspensions. The various administration rates produced 90 percent or greater kill of the larvae for 3, 4, 5 and 6 days respectively.

Isopropyl 2-chlorodifluoromethyl-4-nitro-6-trifluoromethyl-1-benzimidazolecarboxylate was administered at only one rate, 35 mg./kg., as a suspension in sorbitan monolaurate. Ninety percent or more of the larvae were killed by the calf's blood for five successive days.

In the tests of this example, the parasites were exposed to the treated animal's blood indirectly, instead of directly by feeding the parasites on the animal. The control obtained, however, is obviously as significant as if the parasites had sucked blood directly from the animal. The value of the method in protecting animals from the very injurious parasite, the blowfly, is clearly demonstrated by the tests, since several days of parasite control were obtained from a single administration of a compound of this invention.

I claim:
1. A method of killing insect and acarina parasites which consume living tissues of a host animal which comprises orally or percutaneously administering to a host animal infested with such parasites a parasiticidally-effective amount of a compound of the formula

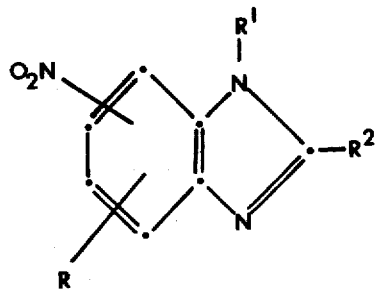

wherein R represents
chloro,
trifluoromethyl,
difluoromethyl, or
chlorodifluoromethyl;
$R^1$ represents
hydrogen,
hydroxy,

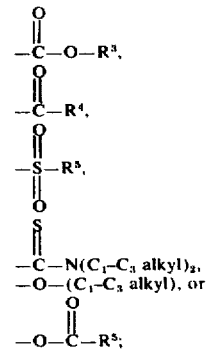

$R^2$ represents
chlorodifluoromethyl,
trifluoromethyl,
1,1,2,2-tetrafluoroethyl,
pentafluoroethyl,
heptafluoropropyl, or
heptafluoroisopropyl;
$R^3$ represents
$C_1$–$C_6$ alkyl,
$C_2$–$C_3$ alkenyl,
phenyl, or
benzyl;
$R^4$ represents
$C_1$–$C_5$ alkyl,
phenyl,
chlorophenyl,
anisyl, or
tolyl;
$R^5$ represents
$C_1$–$C_3$ alkyl, or
phenyl;

or the ammonium, alkali metal, or alkaline earth metal salts of the above compounds wherein R¹ represents hydrogen.

2. The method of claim 1 in which the compound is phenyl 4-nitro-2,6-bis(trifluoromethyl)-1-benzimidazolecarboxylate.

3. The method of claim 1 in which the compound is isopropyl 4-nitro-2,6-bis(trifluoromethyl)-1-benzimidazolecarboxylate.

4. The method of claim 1 in which the compound is 2-chlorodifluoromethyl-4-nitro-6-trifluoromethylbenzimidazole.

5. The method of claim 1 in which the compound is 1-ethoxy-4-nitro-2-pentafluoroethyl-6-trifluoromethylbenzimidazole.

6. The method of claim 1 in which the compound is phenyl 2-chlorodifluoromethyl-4-nitro-6-trifluoromethylbenzimidazolecarboxylate.

7. The method of claim 1 in which the compound is ethyl 2-chlorodifluoromethyl-4-nitro-6-trifluoromethyl-1-benzimidazolecarboxylate.

8. The method of claim 1 in which the compound is isopropyl 4-nitro-2-(1,1,2,2-tetrafluoroethyl)-6-trifluoromethyl-1-benzimidazolecarboxylate.

9. The method of claim 1 in which the compound is 1-hydroxy-4-nitro-2-(1,1,2,2,-tetrafluoroethyl)-6-trifluoromethylbenzimidazole.

10. The method of claim 1 in which the compound is 4-nitro-2-(1,1,2,2-tetrafluoroethyl)-6-trifluoromethylbenzimidazole.

11. The method of claim 1 in which the compound is 2-chlorodifluoromethyl-4-nitro-6-trifluoromethylbenzimidazole.

12. The method of claim 1 in which the compound is 1-methoxy-4-nitro-2-(1,1,2,2-tetrafluoroethyl)-6-trifluoromethylbenzimidazole.

13. The method of claim 1 in which from about 1 mg./kg. to about 100 mg./kg. of the compound is administered to the host animal.

14. The method of claim 13 in which from about 2.5 mg./kg. to about 50 mg./kg. of the compound is administered to the host animal.

15. The method of claim 13 in which the administration is percutaneous.

16. The method of claim 15 in which the compound is administered in an implant.

* * * * *